United States Patent [19]

Imai et al.

[11] Patent Number: 4,540,548

[45] Date of Patent: Sep. 10, 1985

[54] METHOD OF DETECTING FLUORESCENT MATERIALS AND APPARATUS FOR THEIR DETECTION

[75] Inventors: Kazuhiro Imai; Tamura Zenzo, both of Tokyo; Kobayashi Shin-Ichiro, Saitama, all of Japan

[73] Assignee: Yamanouchi Pharmaceutical Co., Ltd., Tokyo, Japan

[21] Appl. No.: 499,417

[22] Filed: Jun. 2, 1983

Related U.S. Application Data

[60] Continuation of Ser. No. 292,487, Aug. 13, 1981, , which is a division of Ser. No. 80,294, Oct. 1, 1979, abandoned.

[30] Foreign Application Priority Data

Apr. 3, 1979 [JP] Japan .................................. 55-39922

[51] Int. Cl.$^3$ ...................... G01N 31/08; G01N 21/76
[52] U.S. Cl. ......................................... 422/52; 422/70
[58] Field of Search ............... 422/52, 68, 70; 436/89, 436/161; 250/361.1 C, 304

[56] References Cited

U.S. PATENT DOCUMENTS

| | | | |
|---|---|---|---|
| 3,334,969 | 8/1967 | Catravas | 436/89 |
| 3,649,203 | 3/1972 | Schneider | 436/89 |
| 3,797,999 | 3/1974 | Witx et al. | 422/52 |
| 3,915,648 | 10/1975 | Stein | 422/52 |
| 4,099,920 | 7/1978 | Heiss | 422/52 |
| 4,160,818 | 7/1979 | Smith et al. | 23/230 B |
| 4,297,273 | 10/1981 | Buckler et al. | 436/805 |
| 4,329,316 | 3/1982 | Wladimiroff | 422/52 |

*Primary Examiner*—Michael S. Marcus
*Assistant Examiner*—Michael S. Gzybowski
*Attorney, Agent, or Firm*—Burgess, Ryan & Wayne

[57] ABSTRACT

A method for detecting fluorescent materials in liquid chromatography. Fluorescent materials are excited by chemical reaction with chemical reagents to yield light (chemiluminescence) and detected at high sensitivity. The detection apparatus is composed of a mixer for mixing a solution containing separated fluorescent materials and solutions of chemical reagents to afford chemiluminescence, a flow cell and a light receptive detection means for detecting the light thus produced.

2 Claims, 3 Drawing Figures

(1) $4 \times 10^{-13}$ MOLE DANSYL-GLUTAMIC ACID (2) $4 \times 10^{-13}$ MOLE DANSYL-ALANINE (3) $4 \times 10^{-13}$ MOLE DANSYL-METHIONINE (1) DANSYL-GLUTAMIC ACID (2) DANSYL-ALANINE (3) DANSYL-METHIONINE

4,540,548

METHOD OF DETECTING FLUORESCENT MATERIALS AND APPARATUS FOR THEIR DETECTION

This application is a continuation of application Ser. No. 292,487, filed Aug. 31, 1981 which is a division of application Ser. No. 80,294, filed Oct. 1, 1979, now abandoned.

BACKGROUND OF THE INVENTION

1. Field of the Invention

This invention relates to a method of detecting fluorescent materials and also an apparatus for their detection. More particularly, the invention relates to a method and apparatus for detecting fluorescent materials at high sensitivity in liquid chromatography by exciting fluorescent materials to produce light by chemical reaction with chemical reagents.

2. Description of the Prior Art

Liquid chromatography is widely used for separating and quantitatively analyzing one or several kinds of materials in a mixture of various components. When the material or materials to be separated and quantitatively analyzed have absorptions in the ultraviolet or visible wavelength region, an absorptions spectrophotometer is usually used as the detection means in liquid chromatography. However, when a higher sensitivity is required, for example, in the case where the amount of the aforesaid material or materials to be analyzed in the sample mixture is very small, a fluorescence detector is employed as the detection means in liquid chromatography.

A conventional fluorescence detector for liquid chromatography is composed of a flow cell through which a solution containing separated fluorescent material is passed, a light source for exciting the fluorescent material, and a light-receptive detection means for perceiving and multiplying the light (fluorescence) generated (Instrumental liquid chromatography p. 81, ed by N. A. Paris, Elsevier Scientific Publishing Comp. 1976). In the conventional fluorescence detector, undesirable phenomena, such as the stray light phenomenon wherein a part of light from the light source, for exciting the fluorescent materials, enters the light-receptive detector and a deviation of the light from the light source induces a deviation in the fluorescence. Thus, an attempt to increase the sensitivity of the detector leads to, at the same time, an increase in the noise level and it is difficult to increase the signal to noise ratio (S/N). In such a fluorescent detector, there is a limitation in the increment of the detection sensitivity and thus the detector is insufficient for the detection of a very minute amount of fluorescent materials.

On the other hand, a means for increasing the sensitivity, has been developed in which without using a flow cell for reducing stray light, special light (strong laser light is applied onto a droplet of the eluate from the column for liquid chromatography to excite the fluorescent materials, but the precision is low and the cost of the apparatus is very high. Therefore, the development of a method wherein fluorescent materials can be detected with high sensitivity and high precision using an inexpensive apparatus has been desired.

SUMMARY OF THE INVENTION

Accordingly, on noticing the principle that fluorescent materials can be chemically excited to give light (chemiluminescence) with chemical reagents, the inventors have tried to apply the aforesaid principle to a detection means for liquid chromatography and investigated in detail the selection and the mixing ratio of solvents used for the chemical reaction for chemiluminescence, the concentration of an oxalic acid derivative and a peroxide which are chemical reagents, an the influence of catalyst using dansylamino acids as representatives for fluorescent materials. As the result thereof it has been found that a very minute amount of a fluorescent material can be quantitatively analyzed by mixing a solution containing separated fluorescent materials and solutions of chemical reagents to cause chemiluminescence and detecting the light. Furthermore, as the result of earnest investigations for further increasing the detection sensitivity, the detecting apparatus as shown schematically in FIG. 1 of the accompanying drawings has been developed and the invention has been accomplished.

According to this invention there is provided a method, for liquid chromatography, of detecting fluorescent materials which are chemically excited to give light with chemical reagents.

Also, according to another embodiment of this invention, there is provided an apparatus for detecting fluorescent materials having no light source in a liquid chromatographic means, comprising a mixer for mixing a solution containing separated fluorescent material or materials and solutions of chemical reagents for chemiluminescence, a mixing coil if necessary, a flow cell through which the above mixed solution passes and a light receptive detection means for detecting the light produced by the chemical reaction.

DESCRIPTION OF THE PREFERRED EMBODIMENTS

Figure 1:
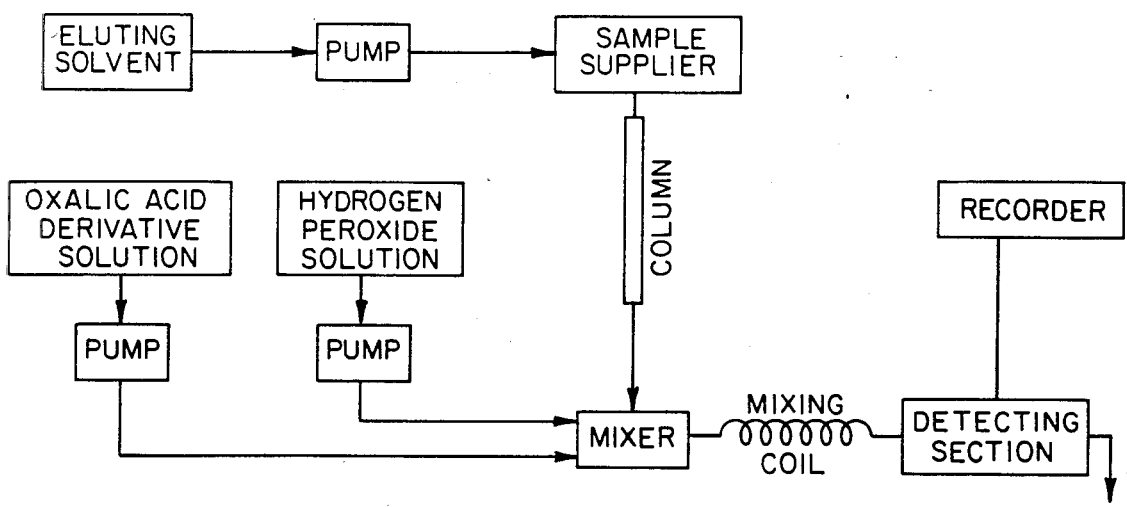
FIG. 1 is a block diagram showing schematically the detection method and apparatus of this invention.

The term "fluorescent material" which is quantitatively detected in this invention means not only a fluorophore, i.e., a material which emits fluorescent light on irradiation with exciting light (visible light or ultraviolet light) but also a fluorescent derivative which can be made to emit fluorescent light, which is formed by the reaction of a non-fluorescent material with some reagent. Practical examples of fluorophores are polycyclic aromatic hydrocarbons such as benzpyrene, etc.; biogenic amines; vitamins such as vitamin $B_2$, vitamin $B_{12}$, vitamin E, etc.; and medicaments such as salicylic acid, etc. Fluorescent derivatives, are materials obtained by reacting non-fluorescent materials such as aminoacids, peptides, proteins, biogenic amines (for example, catecholamines), etc., with a fluorescent reagent such as dansyl chloride, fluorescamine, o-phthalaldehyde, etc.

Therefore, when the material separated and quantitatively determined in this invention is a fluorophore, the material is separated as it is by liquid chromatography and then quantitatively determined by the detection apparatus. On the other hand, when the material is a non-fluorescent material, the material can be converted into a fluorescent derivative prior to the separation by liquid chromatography and quantitatively analyzed after being separated by liquid chromatography, or the material can be subjected to a derivatization reaction after being separated by liquid chromatography to form a fluorescent derivative and then quantitatively determined. Accordingly, the term "a solution containing separated fluorescent materals" in this invention means both the column eluate containing the aforesaid fluorophore or fluorophores, or the fluorescent derivative or derivatives and the solution of the fluorescent derivative or derivatives obtained by converting the non-fluorescent material or materials separated by column into fluorescent derivative or derivatives.

In addition, as a means for exciting a fluorescent material, a method by chemical reaction without need of light irradiation is known as shown below (see, M. Rauhut et al; "J. Am. Chem. Soc." 89, 6515(1967)):

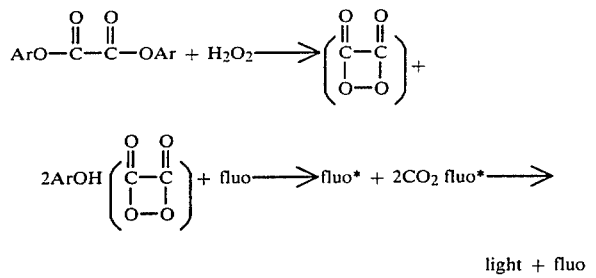

Also, a method wherein both a solution of an oxalic acid ester and a solution of hydrogen peroxide are sprayed on a thin-layer chromatogram to yield chemiluminescence from fluorescent material separated by thin-layer chromatography and a method wherein hydrogen peroxide is quantitatively analyzed in the presence of oxalic acid ester and a large excess of fluorescent material are known (see, T. G. Curtis et al; "J. Chromatogr.", 134, 343(1977) and D. C. Williams et al; "Anal. Chem.", 48, 1003(1976).

However, the chemical reaction for chemiluminescence has never been utilized for the quantitative detection of a fluorescent material using liquid chromatography. By use of the detection method of this invention, a fluorescent material can be separated and quantitatively determined with higher detection sensitivity compared with that in a conventional detection method for fluorescent material. For example, dansyl amino acids can be detected with about $10^3$ times more sensitivity than that obtainable in a conventional method. The detection method and the detection apparatus of this invention will be explained in more detail by referring to the accompanying drawings.

FIG. 1 is an example of block diagram showing schematically the detection apparatus of this invention. That is, as is clear from FIG. 1, the apparatus of this invention is equipped with a detection system comprising (1) a section for mixing a solution containing the separated fluorescent material or materials and solutions of chemical reagents for chemiluminescence and (2) a section for detecting the light produced by the chemical reaction (that is, a flow cell and a light receptive detection means for perceiving and multiplying the light produced by the chemical reaction for chemiluminescence)

in place of a conventional detection system for liquid chromatography. The solutions of chemical reagents for chemiluminescence are sent to the aforesaid mixing section (FIG. 1) by means of a pump at a constant rate and mixed with the solution containing the separated fluorescent material or materials.

Since the chemiluminescence is influenced by the variance in composition of the reaction solutions, it is necessary in the detection apparatus of this invention to keep the ratio of the three solutions, that is, a solution containing the separated fluorescent material or materials, a solution of an oxalic acid derivative, and a solution of peroxide, passing throught a flow cell at a constant value and for the purpose it is desirable to use a syringe type pump giving no pulsating current for transferring each solution. However, when a reciprocating pump is used for reasons of pressure resistance, etc., the detection apparatus of this invention may be practiced by providing a means of eliminating the pulsating current.

In order to obtain emitted light with good reproducible intensity, it is necessary to perform the reaction for chemiluminescence under the conditions wherein each solute and solution are mixed uniformly. For this reason, in the detection apparatus of this invention, it is prefered to use a mixer for promoting the mixing of the aforesaid three kinds of solutions at the zone where the solutions join, and further when mixing of the solutions is insufficient by the use of such a mixer, it is preferable to use a mixing coil having a sufficient length to uniformly mix the solutions before they reach the flow cell. In addition, in the embodiment shown in FIG. 1, a solution containing the separated fluorescent material or materials and two kinds of solutions of chemical reagents for chemiluminescence are simultaneously introduced into a mixer, but pre-mixed solutions of the chemical reagents may be introduced into the mixer through a single conduit-line.

Since in the detection apparatus of this invention a light source for exciting fluorescent material is unnecessary, the influence of the light source on the sensitivity in a conventional fluorescence detector is removed and it is possible to allow a flow cell to come as close as possible to the light-receptive detection means and detect the light emitted from the fluorescent material over the whole spectrum of wavelengths. Furthermore, the flow cell and the light-receptive detection means which are used conventionally can be employed in this invention but it is preferred that they be so constructed that the light generated by the chemical reaction for chemiluminescence can be effectively detected.

An oxalic acid derivative which is one component of the chemical reagents for chemiluminescence used in this invention is a material which brings a fluorescent material into an excited state to give light under the reaction with another component, i.e., a peroxide. Practical examples of the oxalic acid derivatives are an oxalic acid ester, an oxalic acid chloride, an oxalic acid anhydride, oxalic acid amide, etc., (see, M. M. Rauhut et al; "J. Am. Chem. Soc." 89, 6515(1967): ibid., 88, 3604(1966); I. J. Bollyky et al: ibid., 89, 6523(1967); and M. M. Rauhut; "Acc. Chem. Res." 2, 80(1969)). Also, any peroxides (that is, organic peroxide such as performic acid, peracetic acid, perpropionic acid, perbenzoic acid, etc., or inorganic peroxide such as hydrogen peroxide, persulfuric acid, etc.) may be used as the other component but on considering the efficiency for chemiluminescence, etc., hydrogen peroxide is most suitable.

Also, the solvent for dissolving the oxalic acid derivative should be selected on considering the kind and solubility of the oxalic acid derivative used, the stability of the reagent solution, the efficiency for chemiluminescence, etc., but in particular methyl acetate or ethyl acetate is preferred. On the other hand, as a solvent used for the peroxide solution, the same solvent as for the oxalic acid derivative is used when the eluting solvent for liquid chromatography is easily mixed with the solvent for the oxalic acid derivative. However, when an aqueous buffer solution is used as the eluting solvent, an organic solvent which can be uniformly mixed with water, such as methanol, ethanol, acetone, acetonitrile, etc., is selectively used in order to aid the uniform mixing of the solvents.

The conditions such as the mixing ratio of solutions, etc., are properly selected on considering the solvents used and the efficiency for chemiluminescence.

Figure 2:
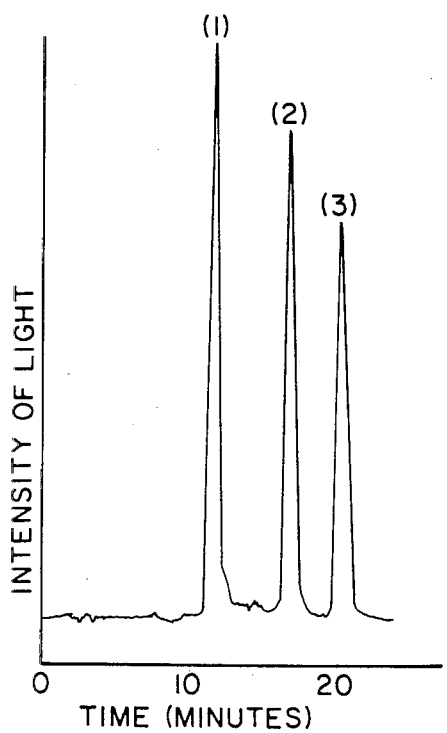
FIG. 2 is a chromatogram obtained by applying this invention to a standard mixed solution of 3 kinds of $4 \times 10^{-13}$ mole dansylamino acids.

An example of separating and quantitatively determining a mixed sample of 3 kinds of dansylamino acids by the detection method of this invention is shown in FIG. 2.

The analysis of dansylamino acids has been performed by liquid chromatography equipped with a conventional fluorescence detector but up to the detection limit reported required an amount of dansylamino acids reported to be about $3 \times 10^{-11}$ mole (Hiroshi Wada et al; "Kagaku no Ryoiki", an extra supplement, 114, 1(1976)) and in an ordinary analysis, it is said that dansylamino acid of the order of $10^{-10}$ to $10^{-9}$ mole is necessary (T. Seki et al; "J. Chromatogr.", 102, 251(1974)).

On the other hand, as is clear from the example shown below, in the detection apparatus of this invention the calibration curve for each dansylamino acid shows good linearity to $5 \times 10^{-14}$ mole from $8 \times 10^{-13}$ mole as the amount injected into liquid chromatography and hence the detection limit is $10^{-14}$ mole ($S/N \approx 2$).

Therefore, according to the detection method of this invention, fluorescent materials such as dansylamino acids can be detected with a good precision at a sensitivity of about $10^3$ times higher than that in a conventional detection method for fluorescent materials by properly selecting the packing for a column and the suitable conditions for chemiluminescence. Thus, almost all fluorescent materials are expected to be detected at a substantially higher sensitivity than that in a conventional detection method.

EXAMPLE

A sample prepared by mixing $4 \times 10^{-13}$ mole of dansyl-glutamic acid, $4 \times 10^{-13}$ mole of dansyl-alanine and $4 \times 10^{-13}$ mole of dansyl-methionine was supplied to a column packed with $\mu$-Bonda Pack C-18 (a trade name, made by Waters Co.) and the dansylamino acids were separated and detected. The eluting solvent was 38% acetonitrile-0.05M trishydroxymethylaminomethane-hydrochloric acid buffer solution (pH 7.7) and an ethyl acetate solution of $5 \times 10^{-3}$ mole of 2,4,6-trichlorophenyl oxalate (TCPO) and an acetone solution of $5.5 \times 10^{-1}$ mole of hydrogen peroxide as the chemical reagents for chemiluminescence were used. The flow rates of 0.18 ml./min. of the eluting solvent, 0.5 ml./min. of the ethyl acetate solution of TCPO, and 1.2 ml./min. of the acetone solution of hydrogen peroxide were selected by use of the apparatus as illustrated in FIG. 1. The chromatogram obtained is shown in FIG. 2.

In FIG. 2, (1), (2) and (3) are the peaks of dansyl-glutamic acid, dansyl-alanine and dansyl-methionine, respectively.

Figure 3:
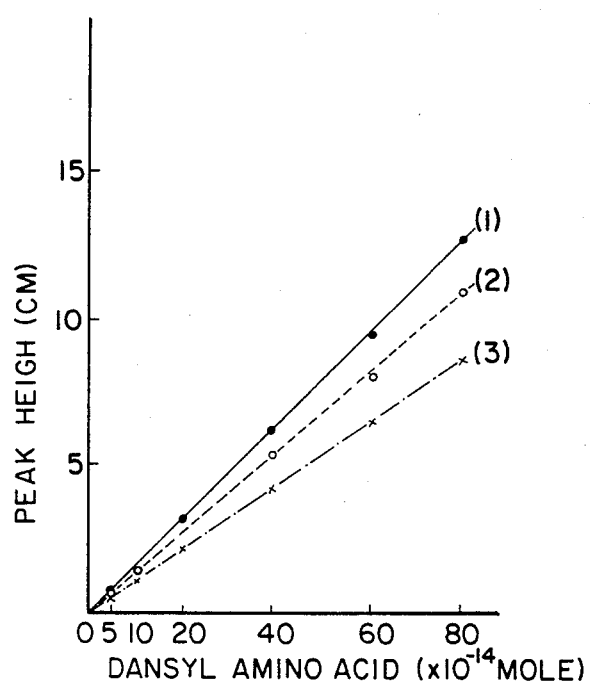
FIG. 3 shows calibration curves for the dansylamino acids aforesaid in each injection amount.

FIG. 3 shows the calibration curves of the abovementioned three dansylamino acids obtained by the chromatogram in each supplied amount. As is clear from the figure, when the peak height of each dansylamino acid is taken on the axis of ordinate and the supplied amount of each dansylamino acid is taken on the axis of abscissa, each calibration curve shows good linearity from $8 \times 10^{-13}$ mole to $5 \times 10^{-14}$ mole, which shows the detection limit being $10^{-14}$ mole ($S/N \approx 2$) as supplied amount.

What is claimed is:

1. In combination, an analytical apparatus for the quantitative determination of a material selected from the group of polycyclic aromatic hydrocarbons, dansylamino acids and vitamins in a mixture comprising:
   (a) means defining and containing a supply of said materials to be separated;
   (b) a liquid column chromatograph for separating said material to form a column eluate containing the separated said material;
   (c) said material separating means in said chromatographic column;
   (d) a first mixing zone;
   (e) means defining and containing a supply of oxalic acid derivative reagent;
   (f) means for passing a solution of an oxalic acid derivative to said first mixing zone at a controlled rate;
   (g) means defining and containing a supply of hydrogen peroxide reagent;
   (h) means for passing a solution of hydrogen peroxide to said first mixing zone at a controlled rate;
   (i) means for simultaneously introducing the separated solution, oxalic acid derivative reagent and hydrogen peroxide into said first mixing means;
   (j) means in said first mixing zone to mix said column eluate, said oxalic acid derivative, and said hydrogen peroxide to form a first mixture;
   (k) a coiled mixing zone through which said first mixture is continuously passed to form a second mixture, whereby chemiluminescence occurs; and
   (l) a light-free detecting section comprising a flow cell and a light receptive detection means for perceiving and multiplying the light produced by the chemiluminescence reaction.

2. The apparatus of claim 1, wherein said means for defining and containing a supply of oxalic acid derivative reagent contains oxalic acid derivatives selected from the group consisting of oxalic acid esters, oxalic acid chlorides, oxalic acid anhydrides and oxalic acid amides.

* * * * *